United States Patent [19]

Vareille et al.

[11] Patent Number: 5,018,863
[45] Date of Patent: May 28, 1991

[54] APPARATUS FOR ANALYSIS BY ELLIPSOMETRY, PROCEDURE FOR ELLIPSOMETRIC ANALYSIS OF A SAMPLE AND APPLICATION TO THE MEASUREMENT OF VARIATIONS IN THE THICKNESS OF THIN FILMS

[76] Inventors: Aimé Vareille, 3 rue Gabriel Didier, 38130 Echirolles; Yves Vuillod, Cidex 237B 5 Lotissement du Coteau, 38790 Crolles; Louis Thevenot, 3, Allee de la Piat, 38240 Meylan (F), all of France

[21] Appl. No.: 319,001

[22] Filed: Mar. 6, 1989

[30] Foreign Application Priority Data

Mar. 4, 1988 [FR] France .................................. 88 02784

[51] Int. Cl.$^5$ ............................................. G01N 21/21
[52] U.S. Cl. .................................................. 356/369
[58] Field of Search ............................... 356/369, 365

[56] References Cited

U.S. PATENT DOCUMENTS 4,176,951 12/1979 Robert et al. .................... 356/365 X

FOREIGN PATENT DOCUMENTS 2365793 4/1978 France .

OTHER PUBLICATIONS

Drevillon et al., "Fast Polarization Modulated Ellipsometer . . .", Rev. Sci. Instrum., vol. 53, No. 7, pp. 964–977, 7/1982.
Patent Abstracts of Japan, vol. 10, No. 101 [P-447] [2158].
Proceedings of the Society of Photo Optical Instrumentation Engineers, vol. 276, 1981, pp. 180–186.
IBM Technical Disclosure Bulletin, vol. 19, No. 11, Apr. 1977, pp. 4134–4137.

Primary Examiner—Davis L. Willis
Assistant Examiner—Matthew W. Koren
Attorney, Agent, or Firm—Nixon & Vanderhye

[57] ABSTRACT

An apparatus for analysis of samples (E) by ellipsometry, and an analysis procedure. The light beam (F) passes through a polarizer (4), a rotating (omega) doubly refracting plate (5) and an analyzer (6). The measurement uses the second and fourth harmonics of the speed of rotation of the plate (5). Application in particular to the growth and etching of thin films.

14 Claims, 2 Drawing Sheets

APPARATUS FOR ANALYSIS BY ELLIPSOMETRY, PROCEDURE FOR ELLIPSOMETRIC ANALYSIS OF A SAMPLE AND APPLICATION TO THE MEASUREMENT OF VARIATIONS IN THE THICKNESS OF THIN FILMS

BACKGROUND OF THE INVENTION

1. Field of the Invention

The invention relates to an apparatus for analysis of a sample by measurement of its ellipsometric parameters, to a procedure for ellipsometric analysis that can be carried out in particular with this apparatus, and to the application of this analyzer or of this procedure to the measurement of variation of thickness of thin films as a function of time, during growth or on the other hand etching of said films.

2. Discussion of Prior Art

The ellipsometric parameters of psi (ellipticity) and delta (phase difference) of an elliptical light vibration can be obtained using a plurality of existing apparatuses. Compared with the invention, they all suffer from the drawbacks of insufficient accuracy or of too slow operation. This latter disadvantage is particularly regrettable in the case of phenomena related to the evolution of thickness of thin films, where measurements every millisecond can be necessary.

For example, an apparatus is known in which a light beam produced by a laser passes through a plane-polarizing plate and a quarter-wave plate before reaching the sample to be analyzed, from which it is reflected before passing through an analyzer and being collected by a photodetector. The ellipsometric parameters are obtained by successive rotation of the polarizer and of the analyzer, when extinction of the light arriving at the photodetector occurs. This apparatus is not intended for rapid measurements, because the set of operations takes about twenty seconds.

A faster apparatus of the same family uses a rotating analyzer, the polarizer remaining immobile. The light collected by the photodetector varies according to a sine wave with two periods per rotation of the analyzer. The ellipsometric parametrers are determined by the ratio of the maximum and minimum amplitudes of the detected light, as well as by the phase of the sine wave.

The measurements with this apparatus are very sensitive to stray light rays that can no longer be recorded, since it is no longer required to bring about extinction of the beam. Another disadvantage is that the apparatus does not directly provide the value of the phase difference delta, but only its sine or cosine depending on whether a quarter-wave plate is used or not; uncertainties occur at the extremums of these circular functions.

Other known apparatuses, using a dichroic sample, for example, suffer from the same disadvantages.

SUMMARY OF THE INVENTION

In contrast, the invention makes it possible to obtain the ellipsometric parameters delta and psi rapidly and accurately. It consists of an apparatus that performs a measurement of light intensity as a function of the rotation of a rotating device that splits the light beam into two waves of different phase, and more particularly of the intensities corresponding to the second and fourth harmonics of this rotation.

The apparatus according to the invention is more precisely an apparatus for analysis of samples by ellipsometry, comprising a source of a light beam, the light beam passing through a plane-polarizing plate and through an analyzer and ending at a measuring set-up after having passed through the sample, the sample being placed between the plane-polarizing plate and the analyzer, wherein it also comprises at least one element for splitting the beam into two waves of different phase between the plane-polarizing plate and the sample, the light beam passing through the elements for splitting the beam, and the elements for splitting the beam rotating in unison, at an angular frequency omega around an axis that is substantially coaxial with the light beam.

According to another characteristic of the invention, by considering that the light intensity on emergence from the analyzer has a constant component of amplitude H0, a component of angular frequency 2 omega and amplitude H2 and a component of angular frequency 4 omega and amplitude H4, the following equations are used:

$$H2 = rs \cdot rs^* \cdot \sin(2A) tg\psi \sin\Delta \sin(b) \sin(2u - 2R - 2P)$$

$$H4 = (\tfrac{1}{4}) rs \cdot rs^* \cdot \{[tg^2\psi - 1 + \cos(2A)(tg^2\psi + 1)][1 - \cos(b)] \cdot \cos(4u - 2P) + \sin(2A) tg\psi \cos\Delta[1 - \cos(b)] \sin(4u + 2R - 2P)\}$$

where rs denotes the complex reflection coefficient of the sample E perpendicualr to the plane of incidence* the complex conjugate, A and P the angles of the directions of polarization of the analyzer and of the polarizer with respect to the plane of incidence, u the variable angle of the fast axis of the doubly refracting plates with respect to the plane of incidence, and b and R the phase difference and the optical rotation introduced by the doubly refracting plates. The comparison of H2 and H4 in amplitude and phase yields the values of psi and delta by inversion of those equations.

Preferably, the elements split the beam into two waves that have a phase difference of about one quarter wave. Doubly refracting plates can be employed.

The invention also consists of a procedure for analyzing a sample by ellipsometry by passing therethrough a polarized light beam that has previously passed through a rotating device that splits it into two waves of different phase, wherein it consists in collecting, separating and measuring the intensity of two periodic light components having two and four periods per rotation of the device for splitting the beam. An analysis can be effected by rotation of the device, and this is very advantageous for measurement on samples the thickness of which varies rapidly with time due to growth or to etching.

BRIEF DESCRIPTION OF THE DRAWINGS

The invention will now be described in more detail by means of the following figures, which are appended for illustrative and in no way limitative purposes.

DETAILED DESCRIPTION OF PREFERRED EMBODIMENTS

Figure 1:
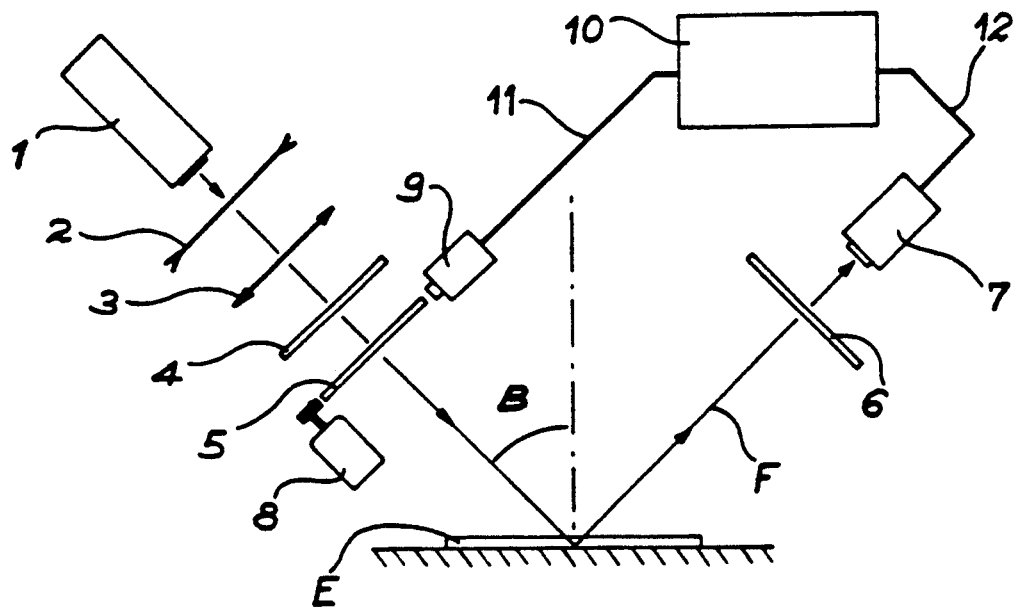
FIG. 1 represents a general schematic diagram of the invention.

FIG. 1 first of all represents a neon-helium laser 1 that emits a monchromatic light beam F. The light beam F passes successively through a lens 2 that focusses the light beam F on a sample E to be measured, a circularly polarizing plate 3 that permits adjustment of the light intensity, a plane-polarizing plate 4 and a doubly refracting plate 5 before reaching the sample E, which it tranverses before being reflected, thereafter passing through an analyzer 6 that plane-polarizes and being collected and measured by a photodetector 7.

The doubly refracting plate 5 rotates under the action of a motor 8 at a constant angular velocity omega; the pass band of the photodetector 7 extends at least between the continuum and the frequency of 8 omega/2 pi. A coder 9 detects graduations on the edge of the doubly refracting plate 5 and then sends measurement command signals to a central system 10 via a line 11; at these instants, the central system 1, via a line 12, measures the light being received by the photodetector 7.

The light beam F reaches the sample E at an angle of incidence theta of about 70°.

Figure 2:
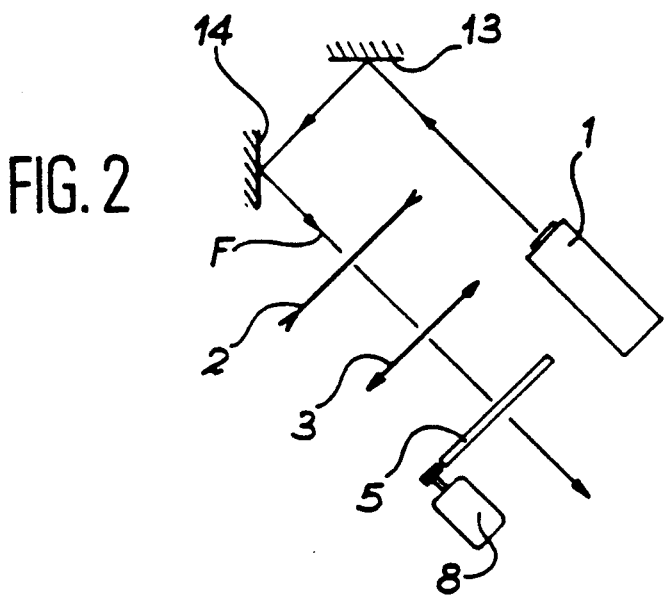
FIG. 2 represents a general schematic diagram of another embodiment of the invention.

The arrangement of FIG. 2 differs from that of FIG. 1 between the laser 1 and the focussing lens 2: two perpendicular mirrors 13 and 14 reflect the light beam F in this zone, so that it is possible to position the laser 1 close to the motor 8 in particular, the beam F emerging from the laser 1 being oriented in the direction opposite to that of the sample E.

In this way there is obtained a more compact, doubled-back device, that otherwise is the exact equal of that of FIG. 1 in terms of its constitution and operation.

Figure 3:
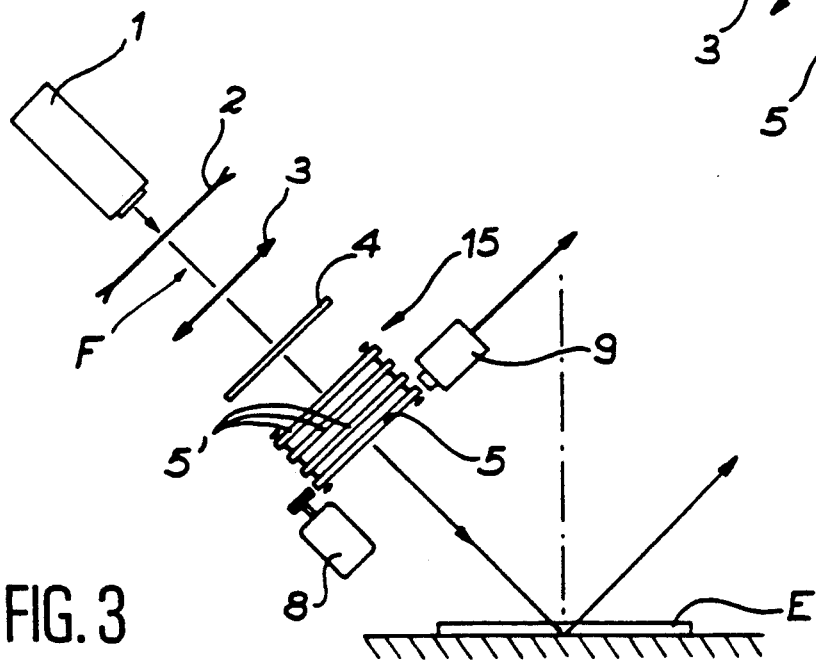
FIG. 3 represents a general schematic diagram of a third embodiment of the invention.

The device of FIG. 3 differs from that of FIG. 1 in that it contains a plurality of supplementary doubly refracting plates 5', that are stacked above the doubly refracting plate 5 and associated therewith by a connecting system 15, and that are therefore also driven rotationally by the motor 8 at the angular velocity omega.

This stack of doubly refracting plates 5 and 5' is optically equivalent to optical rotation followed by double refraction, but the characteristics thereof must be adjusted. In particular, it is easier to obtain a phase difference of one quarter wave between the two vibrations produced by double refraction, and this is advantageous for the accuracy of the measurements.

Figure 4:
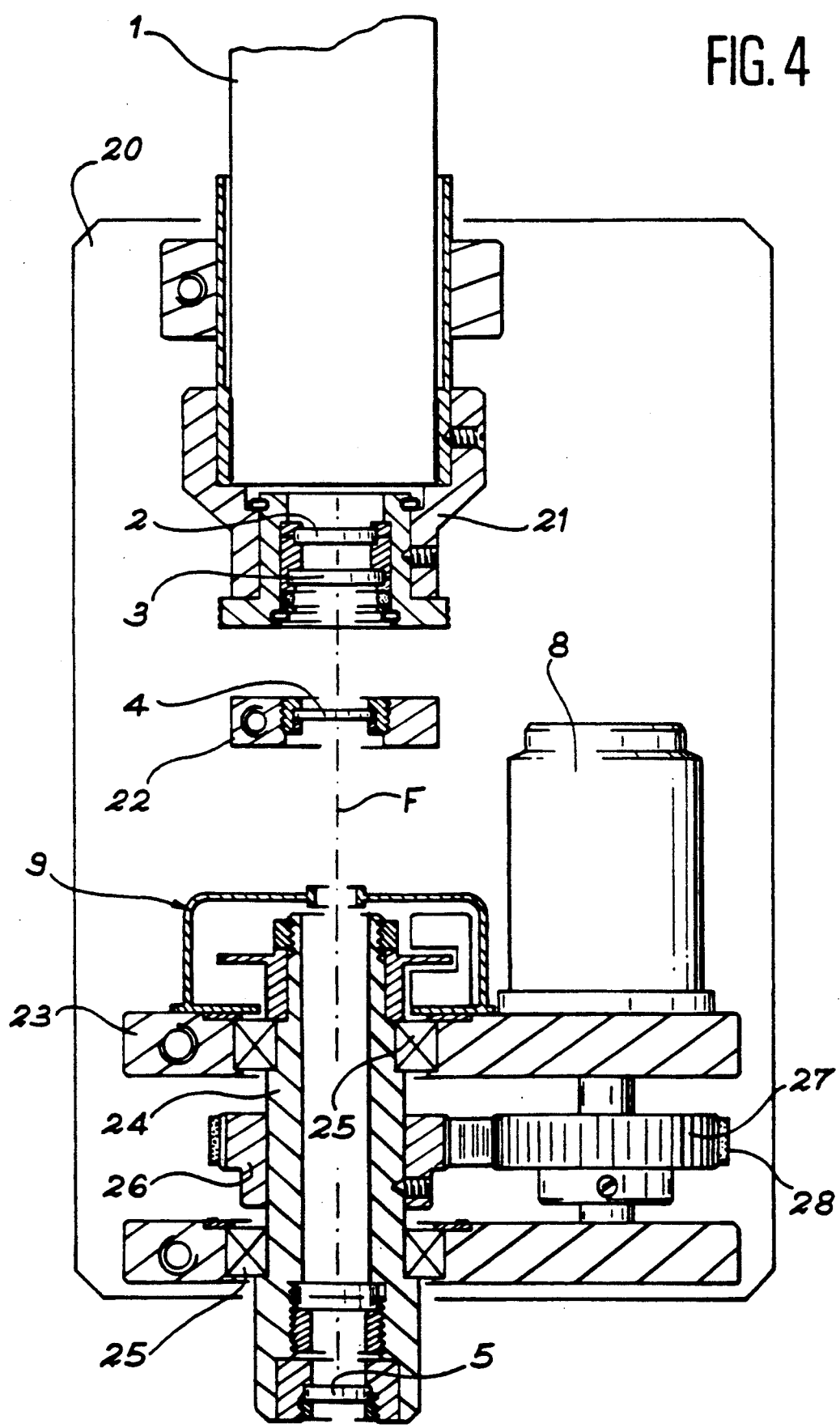
FIG. 4 represents a more practical drawing of part of the device of FIG. 1.

According to FIG. 4, the laser 1 is fixed rigidly on a frame 20 and is provided with a first support 21 that holds the focussing lens 2 and the circularly polarizing plate 3. A second support 22 attached to the frame 20 holds the plane-polarizing plate 4 and permits easy access thereto for possible orientation thereof. A third support 23, attached to the frame 20, holds the motor 8, the coder 9 and a hollow shaft 24 that holds the doubly refracting plate or plates 5 and 5'. The hollow shaft 24 rotates in the third support 23 by the intermediary of two rolling bearings 25, and it holds a take-off pinion 26 that the motor 8 drives by the intermediary of a driving pinion 27 and a synchronous belt 28. The beam F passes along the cavity of the shaft 24.

A description will now be given of how the apparatus functions. The first step consists in orienting the analyzer 6 so as to obtain the most intense possible light componenet in the second harmonic. The sample E is then replaced by a reference sample adapted to this adjustment, such as a slice of thermal silica having a thickness of 100 nanometers.

The measurement itself proceeds as follows: the motor 8 is turned on and the central system periodically receives the signals provided by the photodetector 7. The light intensity on emergence from the analyzer 6 contains a constant component of amplitude H0, a componenet of angular frequency 2 omega and amplitude H2 and a component of angular frequency 4 omega and amplitude H4.

It is demonstrated that:

$$H2 = rs \cdot rs^* \cdot \sin(2A) tg\psi \sin\Delta \sin(b) \sin(2u - 2R - 2P)$$

$$H4 = (\tfrac{1}{4})rs \cdot rs^* \cdot \{[tg^2\psi - 1 + \cos(2A)(tg^2\psi + 1)][1 - \cos(b)] \cdot$$

$$\cos(4u - 2P) + \sin(2A)tg\psi\cos\Delta[1 - \cos(b)]\sin(4u + 2R - 2P)\}$$

where rs denotes the complex reflection coefficient of the sample E perpendicular to the plane of incidence, * the complex conjugate, A and P the angles of the directions of polarization of the analyzer 6 and of the polarizer 4 with respect to the plane of incidence (plane of FIGS. 1 to 3), u the variable angle of the fast axis of the doubly refracting plates 5 and 5' with respect to the plane of incidence, and b and R the phase difference and the optical rotation introduced by the doubly refracting plates 5 and 5'.

The comparison of H2 and H4 in amplitude and phase yields the desired values of psi and delta.

Obviously psi is known by its tangent, i.e., by a function that has no extremum and that therefore does not permit a large uncertainity in psi, whereas delta appears simultaneously in its cosine and its sine, so that the same beneficial effect is obtained. The omission of the amplitude H0 permits independence from the influence of stray light while permitting more measurements per unit time.

The apparatus described in this text can be used in reflectometry, polarimetry, photoelasticity measurement and also in ellipsometry of thin films, in order to follow their growth or their etching as the case may be.

Devices other than the doubly refracting plate or plates 5 and 5' can be employed, for example totally reflecting prisms such a Fresnel rhombohedrons, provided they produce the same effect of splitting the light beam into two waves of different phase. The apparatus can also contain elements that exhibit dichroism, because the preceding equations can be obtained even if the elements for splitting the light beam cause only partial polarization.

The light source can be one that emits nonmonochromatic light. In that case a filter will be interposed at any desired position of the light beam F for analyzing and obtaining monochromatic light.

The described apparatus has an additional advantage that consists in the ability to be calibrated without exact knowledge of the angles A, P and u at the beginning. For this purpose, there is used a calibration sample E having a variable thickness or a series of different thicknesses, from 50 to 100 nanometers, for example, and a series of measurements of the ellipsometric parameters is made for different thicknesses of the calibration sample using the equations descirbed above together with approximate knowledge of the angles A, P and u.

The shape of the curves of the values of psi and delta as a function of thickness is compared to curves that are admissible with the calibration sample and are calculated analytically. The comparison of the experimental curves and the admissible curves yields the errors in the evaluation of the angles A, P and u.

The true values of these angles are then used in the equations for H2 and H4 when the measurements on the real samples are made. Tedious manual adjustments of the position of the optical elements, as are often necessary with the known apparatuses, are dispensed with.

What is claimed is:

1. An apparatus for analysis of a sample by ellipsometry, comprising:
   a source of a light beam having a beam path toward said sample;
   a plane-polarizing plate on said beam path between said source and said sample;
   a measuring setup located along said beam path after said light beam has encountered said sample;
   an analyzer located along said beam path between said sample and said measuring setup;
   at least one element, located between said source and said sample, for splitting the beam into two waves of different phase; means for rotating said at least one element for splitting the beam around an axis that is substantially coaxial with the light beam at a frequency ω, said measuring setup including means responsive to components of said light beam at 2ω and 4ω.

2. An apparatus for analysis by ellipsometry according to claim 1, wherein the elements for splitting the beam are doubly refracting plates.

3. An apparatus for analysis by ellipsometry according to claim 2, wherein the elements split the beam into two waves having a phase difference of about one quarter wave.

4. An apparatus for analysis by ellipsometry according to claim 2, wherein it contains a lens focussing the light beam on the sample.

5. An apparatus for analysis by ellipsometry according to claim 1, wherein the light beam is reflected, between the source and the sample, by mirrors.

6. A procedure for analyzing a sample by ellipsometry in order to determine two ellipsometry parameters, comprising the steps of:
   passing a polarized light beam through a rotating device that rotates at a frequency ω and that splits said light beam into two waves of different phase;
   passing said light beam through said sample;
   collecting and separating two periodic light components having frequencies of 2ω and 4ω and calculating said ellipsometry parameters by comparing the intensities and phases of both light components without annuling the periodic light component having a frequency of 2ω.

7. A procedure for analyzing a sample by ellipsometry according to claim 6, wherein it uses an apparatus in which the beam passes successively through a plane-polarizing plate, the device for splitting the beam, the sample and an analyzer and wherein it uses the equations:

$$H2 = rs \cdot rs^* \cdot \sin(2A) tg\psi \sin\Delta \sin(b) \sin(2u - 2R - 2P)$$

$$H4 = (\tfrac{1}{4}) rs \cdot rs^* \cdot \{[tg^2\psi - 1 + \cos(2A)(tg^2\psi + 1)][1 - \cos(b)] \cdot$$

-continued
$$\cos(4u - 2P) + \sin(2A) tg\psi \cos\Delta[1 - \cos(b)]\sin(4u + 2R - 2P)\}$$

where rs denotes the complex reflection coefficient of the sample perpendicular to the plane of incidence, * the complex conjugate, A and P the angles of the directions of polarization of the analyzer and of the polarizer with respect to the plane of incidence, u the variable angle of the fast axis of the doubly refracting plates constituting the device for splitting the beam, and b and R the phase difference and the optical rotation introduced by the doubly refracting plates.

8. A procedure for analyzing a sample by ellipsometry according to claim 7, wherein it contains a preliminary calibration step comprising:
   approximately adjusting the angles of the directions of polarization of the analyzer and of the polarizer as well as the angle of the fast axis of the doubly refracting plates;
   carrying out measurements by ellipsometry using the equations for a calibration sample;
   comparing the measurements with theoretically admissible results to deduce therefrom information for correction of the values of adjustment of the angles, and
   correcting the values of adjustment of the angles used in the equation by means of said information.

9. A procedure for analyzing a sample by ellipsometry according to claim 6, wherein the sample is a thin film having a thickness that is variable with time.

10. An apparatus for analysis of a sample by ellipsometry in order to yield two ellipsometry parameters, comprising:
    a source of a light beam having a beam path toward said sample;
    a plane-polarizing plate on said beam path between said source and said sample;
    a measuring setup located along said beam path after said light beam has encountered said sample;
    and analyzer located along said beam path between said sample and said measuring setup;
    at least one element, located between said source and said sample, for splitting the beam into two waves of different phase; means for rotating said at least one element for splitting the beam around an axis that is substantially coaxial with the light beam at a frequency ω, said measuring setup including means responsive to components of said light beam at 2ω and 4ω and for calculating said two ellipsometry parameters by comparing the intensities and phases of both light beam components.

11. An apparatus for analysis by ellipsometry according to claim 10, wherein the elements for splitting the beam are doubly refracting plates.

12. An apparatus for analysis by ellipsometry according to calim 11, wherin the elements split the beam into two waves having a phase difference of about one quarter wave.

13. An apparatus for analysis by ellipsometry according to claim 11, wherein it contains a lens focussing the light beam on the sample.

14. An apparatus for analysis by ellipsometry according to claim 10, wherein the light beam is reflected, between the source and the sample, by mirrors.

* * * * *